(12) United States Patent
Hnatowich et al.

(10) Patent No.: US 8,278,247 B2
(45) Date of Patent: Oct. 2, 2012

(54) METHODS AND COMPOSITIONS FOR INCREASING THE AMOUNTS OF PHOSPHORUS AVAILABLE FOR PLANT UPTAKE FROM SOILS

(75) Inventors: Garry Lawrence Hnatowich, Saskatoon (CA); Shelagh Jean Steckler, Warman (CA); Mary Elizabeth Leggett, Saskatoon (CA); Kari Lynn Priest, Saskatoon (CA)

(73) Assignee: Novozymes Biologicals Limited, Saskatchewan (CA)

( * ) Notice: Subject to any disclaimer, the term of this patent is extended or adjusted under 35 U.S.C. 154(b) by 178 days.

(21) Appl. No.: 12/571,913

(22) Filed: Oct. 1, 2009

(65) Prior Publication Data

US 2010/0099560 A1  Apr. 22, 2010

Related U.S. Application Data

(60) Provisional application No. 61/102,603, filed on Oct. 3, 2008.

(30) Foreign Application Priority Data

Oct. 1, 2008 (EP) .................................... 08165591

(51) Int. Cl.
*A01N 63/00* (2006.01)
(52) U.S. Cl. ...................................................... 504/117
(58) Field of Classification Search ........................ None
See application file for complete search history.

(56) References Cited

U.S. PATENT DOCUMENTS

| 5,026,417 A | 6/1991 | Kucey |
| 5,770,787 A | 6/1998 | Montague |

FOREIGN PATENT DOCUMENTS

| EP | 0 284 236 | | 9/1988 |
| WO | WO 95/06623 | | 3/1995 |
| WO | WO-9506623 | * | 3/1995 |

OTHER PUBLICATIONS

Asea et al., Inorganic Phosphate Solubilization Culture and Soil (Soil Biol. Biochem., vol. 20, No. 4 pp. 459-464, 1988.*
Wakelin et al., "The Effect of *Penicillium fungi* on Plant Growth and Phosphorus Mobilization in Neutral to Alkaline Soils from Southern Australia", Can. J. Microbiol., vol. 53, pp. 106-115 (2007).
Kucey, "Increased Phosphorus Uptake by Wheat and Field Beans Inoculated with a Phosphorus-Solubilizing *Penicillium bilaji* Strain and with Vesicular-Arbuscular Mycorrhizal Fungi", Applied and Environmental Microbiology, vol. 53, No. 12, pp. 2699-2703 (1987).
Kucey, "Phosphate-Solubilizing Bacteria and fungi in Various Cultivated and Virgin Alberta Soils", Can. J. Soil Sci., vol. 63, pp. 671-678 (1983).
Pandey et al., "Phosphate solubilization by *Penicillium* spp. isolated from soil samples of Indian Himalayan region", World J Microbiol Biotechnol, vol. 24, pp. 97-102 (2008).
Barroso and Nahas, "The status of soil phosphate fractions and the ability of fungi to dissolve hardly soluble phosphates", Applied Soil Ecology, vol. 29, pp. 73-83 (2005).
Tulloch et al., Horticultural Science, vol. 27, No. 6, pp. 846 (PS16) (1992).
Asea et al., "Inorganic Phosphate Solubilization by Two Penicillium Species in Solution Culture and Soil", Soil Bid. Biochem. vol. 20, No. 4, pp. 459-464 (1988).
Kucey, "Effect of *Pénicillium Bilaji* on the Solubility and Uptake of P and Micronutrients From Soil by Wheat", Can. J. Soll .Sel, vol. 68, pp. 261-270 (1988).

* cited by examiner

*Primary Examiner* — Alton Pryor
(74) *Attorney, Agent, or Firm* — Thomas C. Sova, IV

(57) ABSTRACT

The present invention relates to a method of enhancing growth conditions for plants by growing the plants in soil containing, in proximity to the plant roots, both a phosphorus source and at least two strains of the fungus *Penicillium*, particularly *P. bilaiae*, more particularly strains NRRL 50162 and NRRL 50169.

19 Claims, 4 Drawing Sheets

METHODS AND COMPOSITIONS FOR INCREASING THE AMOUNTS OF PHOSPHORUS AVAILABLE FOR PLANT UPTAKE FROM SOILS

CROSS-REFERENCE TO RELATED APPLICATIONS

This application claims priority or the benefit under 35 U.S.C. 119 of European patent application no. EP 08 165 591.2 filed Oct. 1, 2008 and U.S. provisional application No. 61/102,603 filed Oct. 3, 2008, the contents of which are fully incorporated herein by reference.

REFERENCE TO A DEPOSIT OF BIOLOGICAL MATERIAL

This application contains a reference to deposits of biological material, which deposits are incorporated herein by reference. For complete information see last 2 pages of the description.

FIELD OF THE INVENTION

The present invention relates to a method of increasing the availability of phosphorus for plant uptake from soil, to a composition for application to soil and to a plant seed.

BACKGROUND OF THE INVENTION

In order to maintain healthy growth, plants must extract a variety of elements from the soil in which they grow. These elements include phosphorus and the so-called micro-nutrients (e.g. copper, iron and zinc), but many soils are deficient in such elements or they contain them only in forms which cannot be readily taken up by plants (it is generally believed that essential elements cannot be readily taken up by plants unless they are present in dissolved form in the soil).

To counteract such deficiencies, sources of the deficient elements are commonly applied to soils in order to improve growth rates and yields obtained from crop plants. For example, phosphates are often added to soil to counteract a lack of available phosphorus. Phosphate added to the soil as a commercial fertilizer (e.g., mono-ammonium phosphate or triple-superphosphate) is readily plant available, but is rapidly converted in soil to relatively unavailable forms. It has been estimated that only 10 to 30% of phosphate fertilizer is used by the plant in the year it is applied, and one-third to one-half of the phosphate fertilizer applied may never be recovered by the plant.

Attempts have been made in the past to use microorganisms to improve the availability of essential elements in soil systems. In particular species of the fungus *Penicillium* has been used for this purpose. U.S. Pat. No. 5,026,417 describes an isolated strain of *P. bilaiae* which is capable of improving the uptake of phosphorous by plants when applied to the soil.

There is, however, still a need for systems for improving growth conditions for plants, particularly by increasing the levels of available phosphorus in soil systems.

SUMMARY OF THE INVENTION

The present invention is based on the finding that different species of Penicillium, which when applied alone may have varying ability to improve the availability of phosphorus both from insoluble phosphates and from manufactured fertilizers, can when combined give rise to a synergistic effect that surpasses what could be expected from individual results.

In particular this holds true for *Penicillium* species belonging to *P. bilaiae*.

The invention provides in a first aspect a method of increasing the availability of phosphorus for plant uptake from soil, which method comprises introducing into the soil inoculums of at least two different strains of the fungus *Penicillium*.

In a second aspect the invention relates to a method of enhancing growth conditions of plants, which comprises growing the plants in soil containing, in proximity to the plant roots, both a phosphorus source and at least two strains identified by the deposit numbers NRRL 50169 and NRRL 50162.

In a third aspect the invention relates to a composition for application to soil, which comprises: i) inoculums of at least two strains of the fungus *Penicillium*, particularly *P. bilaiae* and/or *P. gaestrivorus*, and ii) a soil-compatible carrier for the fungus.

In a forth aspect the invention relates to a plant seed having a coating comprising inoculums of at least two strains of the fungus *Penicillium*, in particular *P. bilaiae* and/or *P. gaestrivorus*, and a solid soil-compatible carrier therefore.

DETAILED DESCRIPTION OF THE INVENTION

Figure 1:
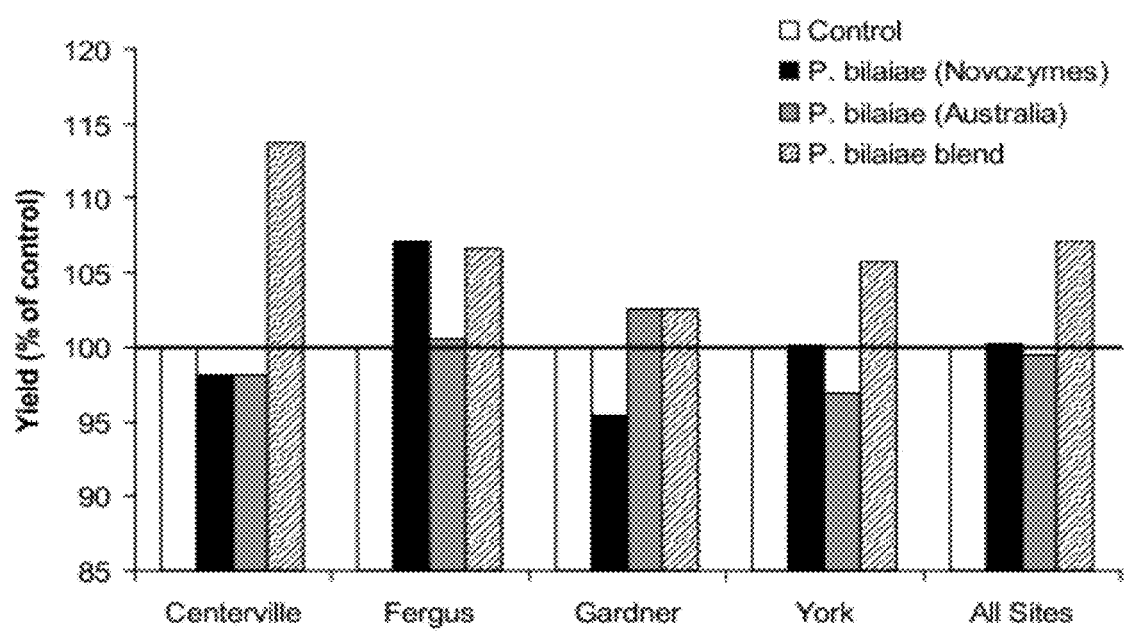
FIG. 1 shows the effect of inoculation with phosphate solubilising micro-organisms on yield of corn. *P. bilaiae* (Novozymes P-201) corresponds to strain NRRL 50169, and *P. bilaiae* (Australia, P-208) corresponds to NRRL 50162.

The fungus *Penicillium bilaiae* is a known micro-organism that has previously been deposited at the American Type Culture Collection in Rockville, Md., USA under the deposit number ATCC 22348 (1974 edition of the ATCC catalogue). In the 1984 catalogue, the same deposit number is used for *P. bilaii* and a further strain is identified by the deposit number 18309.

Further isolates of this fungus has been discovered in soil from a location (latitude 49.degree. 48' N, longitude 113.degree. 6' W) in Southern Alberta, Canada. This strain has previously been shown to improved P-solubilizing activity compared to the earlier strains deposited at the ATCC. A deposit of this improved strain was made at the ATCC under the deposit number 20851 in accordance with the terms of the Budapest Treaty. In this deposit the fungus was named *P. bilaji* and the taxonomic details and it use has been described in U.S. Pat. No. 5,026,417. This strain has now been re-deposited as NRRL 50169. For complete information of the deposit see last page of the description.

The name of this species has subsequently been changed again and is now recognized as *P. bilaiae*. This name will consequently be used throughout the specification.

A new isolate of *P. bilaiae* has been discovered in Australia. It was originally isolated in 2002 from wheat roots and grown in collected soil samples from Coonalpyn in South Australia (Wakelin et al., 2004. Biol Fertil Soils 40:36-43). A deposit of this improved strain was made as deposit number NRRL 50162. For complete information of the deposit see last page of the description and the taxonomic details of this isolate and its proposed use is described in US provisional application filed on Jan. 10, 2008 in the name of CSIRO.

Other *Penicilium* spp. found to be particularly useful according to the present invention are strains of *P. gaestrivorus*. One such strain was isolated in 2002 from wheat roots grown in collected soil samples from New South Wales, Australia (Wakelin et al., 2004. Biol Fertil Soils 40:36-43), and deposited as NRRL 50170. For complete information of the deposit see last page of the description.

According to one aspect the invention relates to a method of enhancing growth conditions of plants, comprising growing the plants in soil containing, in proximity to the plant roots, both a phosphorus source and at least two strains of the fungus *Penicillium*. Particularly the *Penicilium* fungus is selected from *P. bilaiae* and/or *P. gaestrivorus*. In particular the enhanced growth is provided by enhancing the availability of phosphorus for plant uptake from soil.

In a particular embodiment the *Penicillium* strains are selected from the strain deposited as NRRL 50169 and NRRL 50162.

The use of a combination of at least two different Penicillium strains has the following advantages. When applied to soil already containing insoluble (or sparingly soluble) phosphates, the use of the combined fungal strains will result in an increase in the amount of phosphorus available for plant uptake compared to the use of only one *Penicillium* strain. This in turn may result in an increase in phosphate uptake and/or an increase in yield of plants grown in the soil compared to use of individual strains alone. If e.g. phosphorous is not a limiting factor a yield increase may not necessarily follow as a result of the increased availability. The combination of strains also enables insoluble rock phosphates to be used as an effective fertilizer for soils which have inadequate amounts of available phosphorus.

According to one aspect the invention therefore relates to a method of increasing the availability of phosphorus for plant uptake from soil, which method comprises introducing into the soil inoculums of at least two different strains of the fungus *Penicillium*. The presence of the two strains of *Penicillium* will enhance the availability of phosphorus for plant uptake.

The said phosphorus may be provided from a source selected from the group consisting of sources originally present in the soil, sources added to the soil as amendments and combinations thereof.

The term "inoculum" as used in this specification is intended to mean any form of fungus cells, mycelium or spores, which is capable of propagating on or in the soil when the conditions of temperature, moisture, etc., are favorable for fungal growth.

By "source" of a particular element we mean a compound of that element which, at least in the soil conditions under consideration, does not make the element fully available for plant uptake.

In particular the *Penicillium* fungus is selected from the group consisting of *P. bilaiae, P. albidum, P. aurantiogriseum, P. chrysogenum, P. citreonigrum, P. citrinum, P. digitatum, P. frequentas, P. fuscum, P. gaestrivorus, P. glabrum, P. griseofulvum, P. implicatum, P. janthinellum, P. lilacinum, P. minioluteum, P. montanense, P. nigricans, P. oxalicum, P. pinetorum, P. pinophilum, P. purpurogenum, P. radicans, P. radicum, P. raistrickii, P. rugulosum, P. simplicissimum, P. solitum, P. variabile, P. velutinum, P. viridicatum, P. glaucum, P. fussiporus*, and *P. expansum*.

In one particular embodiment the *Penicillium* species is *P. bilaiae*. In another particular embodiment the *Penicillium* species is *P. gaestrivorus*. In a further particular embodiment the at least two strains are one strain of *P. bilaiae* and one strain of *P. gaestrivorus*.

In another particular embodiment the *P. bilaiae* strains are selected from the group consisting of ATCC 20851, NRRL 50169, ATCC 22348, ATCC 18309, NRRL 50162.

In an even further embodiment the at least two strains are NRRL 50169 and NRRL 50162.

In a still further embodiment the at least two strains are NRRL 50169 and NRRL 50170.

In a still further embodiment the at least two strains are NRRL 50162 and NRRL 50170.

The *Penicillium* fungus according to the invention and in particular the specific strains, ATCC20851, NRRL 50169, NRRL 50170 and NRRL 50162 can be grown using solid state or liquid fermentation and a suitable carbon source. *Penicillium* isolates may be grown using any suitable method known to the person skilled in the art. For example, the fungus may be cultured on a solid growth medium such as potato dextrose agar or malt extract agar, or in flasks containing suitable liquid media such as Czapek-Dox medium or potato dextrose broth. These culture methods may be used in the preparation of an inoculum of Penicillium spp. for coating seeds and/or application to carrier to be applied to soil.

Solid state production of Penicillium spores may be achieved by inoculating a solid medium such as a peat or vermiculite-based substrate, or grains including, but not limited to, oats, wheat, barley, or rice. The sterilized medium (achieved through autoclaving or irradiation) is inoculated with a spore suspension ($1\times10^2$-$1\times10^7$ cfu/ml) of the appropriate Penicillium spp. and the moisture adjusted to 20 to 50%, depending on the substrate. The material is incubated for 2 to 8 weeks at room temperature. The spores may also be produced by liquid fermentation (Cunningham et al., 1990. Can J Bot 68:2270-2274). Liquid production may be achieved by cultivating the fungus in any suitable media, such as potato dextrose broth or sucrose yeast extract media, under appropriate pH and temperature conditions (as could be performed by anyone skilled in the art).

The resulting material may be used directly as a seed treatment, or the spores may be harvested, concentrated by centrifugation, formulated, and then dried using air drying, freeze drying, or fluid bed drying techniques (Friesen T., Hill G., Pugsley T., Holloway G., and Zimmerman D. 2005, Experimental determination of viability loss of *Penicillium bilaiae* conidia during convective air-drying Appl Microbiol Biotechnol 68: 397-404) to produce a wettable powder. The wettable powder is then suspended in water, applied to the surface of seeds, and allowed to dry prior to planting. The wettable powder may be used in conjunction with other seed treatments, such as, but not limited to, chemical seed treatments, carriers (e.g., talc, clay, kaolin, silica gel, kaolinite) or polymers (e.g., methylcellulose, polyvinylpyrrolidone). Alternatively, a spore suspension of the appropriate *Penicillium* spp. may be applied to a suitable soil-compatible carrier (e.g., peat-based powder or granule) to appropriate final moisture content. The material is incubated at room temperature for 2 to 8 weeks, and can then be applied to the soil in the furrow along with the seed.

As described above, it has been found that the combination of at least two strains of *Penicillium* increases the amount of phosphorus available for plant uptake from commercial phosphorus fertilizers compared to the use of only one strain so commercial fertilizers may be added to the soil instead of (or even as well as) natural rock phosphate.

According to further embodiments of the invention the source of phosphorous comprises a source of phosphorous native to the soil or in another embodiment the source of phosphorous is added to the soil.

In one embodiment said source is rock phosphate. In another embodiment said source is a manufactured fertilizer.

Commercially available manufactured phosphate fertilizers are of many types. Some common ones are those containing monoammonium phosphate (MAP), triple super phosphate (TSP), diammonium phosphate, ordinary superphosphate and ammonium polyphosphate. All of these fertilizers are produced by chemical processing of insoluble natural rock phosphates in large scale fertilizer-manufacturing facilities and the product is expensive. By means of the present invention it is possible to reduce the amount of these fertilizers applied to the soil while still maintaining the same amount of phosphorus uptake from the soil.

In a further particular embodiment the source or phosphorus is organic. An organic fertilizer refers to a soil amendment derived from natural sources that guarantees, at least, the minimum percentages of nitrogen, phosphate, and potash. Examples include plant and animal by-products, rock powders, seaweed, inoculants, and conditioners. These are often available at garden centers and through horticultural supply companies. In particular said organic source of phosphorus is from bone meal, meat meal, animal manure, compost, sewage sludge, or guano.

Other fertilizers, such as nitrogen sources, or other soil amendments may of course also be added to the soil at approximately the same time as the *Penicillium* fungus or at other times, so long as the other materials are not toxic to the fungus.

Since the fungus has the effect of solubilizing phosphates which may already be present in soil (i.e., those which are native to the soil) and also those which are added to the soil, the fungus may be applied alone to soils which contain native sources of phosphorus, or may be applied to any soils in conjunction with added sources of phosphorus. The inoculums comprising the fungal strains according to the invention can as described above be provided using solid state or liquid fermentation and a suitable carbon source.

The amount of the inoculum to be applied to the soil is not limited in any particular respect. Clearly, if an insufficient amount is used, a noticeable effect will not be obtained. On the other hand, the use of large amounts of the inoculum will be wasteful because the amounts of phosphorus and/or micronutrients made available in the soil reach a maximum at a certain application rate and further additions beyond this rate do not give additional benefits. The suitable application rates vary according to the type of soil, the type of crop plants, the amounts of the source of phosphorus and/or micronutrients present in the soil or added thereto, etc. and a suitable rate can be found without difficulty by simple trial and error experiments for each particular case. Normally, the application rate falls into the range of 0.001-1.0 Kg fungal spores and mycelium (fresh weight) per hectare, or $10^2$-$10^6$ colony forming units (cfu) per seed (when coated seeds are used), or on a granular carrier applying between $1 \times 10^6$ and $1 \times 10^{11}$ colony forming units per hectare. Even though the inoculums used according to the present invention is comprised of a mixture/combination of inoculums of at least two different strains of *Penicillium* it is the total amount of spores or colony forming units in the combined mixture that is referred to throughout the specification.

The fungal cells in the form of e.g. spores and optionally a carrier can be added to a seed row of the soil at the root level or can be used to coat seeds prior to planting. When spores are added to the soil a granular formulation will be preferable. Formulations as liquid, peat, or wettable powder will be suitable for coating of seeds. When used to coat seeds, the material can be mixed with water, applied to the seeds and allowed to dry.

Other carriers for the spores can be used to coat seeds. For example, the spores can be grown on moistened bran, dried, sieved and applied to seeds prior coated with an adhesive, e.g. gum arabic.

The carrier should preferably be a soil compatible carrier. The term "soil-compatible" means any material which can be added to the soil without having an adverse effect on plant growth, soil structure, soil drainage or the like. Suitable carriers comprise, but are not limited to, wheat chaff, bran, ground wheat straw, peat-based powders or granules, gypsum-based granules, and clays (e.g., kaolin, bentonite, montmorillonite).

In a further aspect the present invention relates to a composition comprising at least two strains of the *Penicilium* fungus according to the invention, and a carrier. Suitable carriers include water, aqueous solutions, slurries, solids (e.g. peat, wheat, bran, vermiculite, and pasteurized soil) or dry powders.

The composition according to the invention may suitably be applied in the method of the invention for increasing the availability of phosphorous for plant uptake from soil.

In a particular embodiment the at least two strains of *Penicilium* comprised in the composition are selected from the group consisting of *Penicilium bilaiae* and *Penicilium gaestrivorus*. More particularly the Penicilium strains are selected from the group consisting of NRRL 50169, NRRL 50162, NRRL 50170. In a further specific embodiment the two strains are NRRL 50169 and NRRL 50162. In another embodiment the two strains are NRRL 50162 and NRRL 50170.

Particularly the carrier may in one embodiment comprise a liquid containing a nutrient for the fungus.

In a still further embodiment the present invention relates to a plant seed having a coating comprising inoculums of at least two strains of the fungus *Penicillium*, in particular *P. bilaiae* and/or *P. gaestrivorus*, and a solid soil-compatible carrier therefore. More particularly the *Penicillium* strains are selected from the group consisting of NRRL 50169, NRRL 50162, NRRL 50170. In a further specific embodiment the two strains are NRRL 50169 and NRRL 50162. In another embodiment the two strains are NRRL 50162 and NRRL 50170.

The composition may contain additional additives including buffering agents, wetting agents, coating agents, and abrading agents.

The methods according to the invention are potentially useful for improving growth conditions resulting in increased phosphorous uptake and/or yield for any type of plant. In one particular embodiment the plant is selected from the group consisting of cereals, legumes, *Brassica* spp., fruits, vegetables, nuts, flowers, and turf. Particularly the cereals are wheat, corn, rice, oat, rye, barley. Particularly legumes are lentil, chickpeas, beans, soybeans, peas, and alfalfa.

In another particular embodiment the plants are selected from the group consisting of alfalfa, rice, wheat, barley, rye, oat, cotton, sunflower, peanut, corn, potato, sweet potato, bean, pea, chickpeas, lentil, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

EXAMPLES

Example 1

Characterization of Isolates

Genetic analysis of the D2 region of 28S rDNA has confirmed the two strains ATCC 20851 (P-201 strain; same as NRRL 50169) and NRRL 50162 (P-208 strain) as being *P. bilaiae*, with additional work at CSIRO (Australia) proving them to be different strains. Strains of *P. bilaiae* were sequenced by MIDI Labs in Newark, Del. using universal primers to the D2 region of the 28S rDNA gene. Phylogenetic comparison calculations were done using the program CLUSTAX to align the sequence to other closely related species indicated by an initial BLAST analysis of the sequence. Once the multiple alignment file was created, a Neighbor Joining tree was constructed, and a distance matrix was calculated as the basis for identifying the genus and species of the strain. All alignment and phylogenetics related operations were done in Mega 4.0. Sequences were imported into the Alignment Explorer in Mega, and then aligned using ClustalW. A phylogenetic tree was constructed using bootstrapping to test the robustness.

Identifications of the two strains were confirmed as Penicillium bilaiae according to the following classification:

| | |
|---|---|
| Kingdom | Fungi |
| Subkingdom | *Dikarya* |
| Phylum | *Ascomycota* |
| Subphylum | *Pezizomycotina* |
| Class | *Eurotiomycetes* |
| Subclass | *Eurotiomycetidae* |
| Order | *Eurotiales* |
| Family | *Trichocomaceae* |
| Subfamily | mitosporic (anamorphic) *Trichocomaceae* |
| Genus | *Penicillium* |
| Species | *bilaiae* |

Example 2

Field Trials of Combination Treatment

Field trials were established in 2007 at four USA locations to screen the effect of inoculation with phosphate solubilizing strains of *P. bilaiae* on the harvested yield of corn. Treatments included two strains of *P. bilaiae* singly and in combination as well as an uninoculated control.

The trials were established at four USA locations as randomized complete blocks with 6 replicates per trial. The USA trials were conducted by four independent research firms covering four USA States. The research contractors and locations were Viger Ag Research (Fergus Falls, Minn.), Benson Research (York, Nebr.), Northern Plains Ag (Gardner, N. Dak.), and South Dakota Ag Research (Centerville, S. Dak.).

The trial was composed of four treatments that included two single strain *Penicillium* treatments NRRL 50169 (Novozymes P-201 strain) and NRRL 50162 (Australian P-208 strain), a double strain treatment, and an un-inoculated control. All *Penicillium* strains were formulated as peat granules.

Production of peat granules was achieved by inoculating the substrate with a liquid spore suspension. Cultures of *Penicillium* were taken from storage at −80° C. and grown on potato dextrose agar. Spores were collected by using a glass rod to scrape the surface of a sporulating culture (obtained after two weeks of incubation at room temperature) into sterile water amended with 0.1% v/v Tween 80. The spore suspension of the appropriate *Penicillium* spp. was added to peat granules, which were then mixed thoroughly to achieve a uniform inoculation, stored in plastic-lined paper bags, and incubated for 2 to 8 weeks at room temperature (approximately 22 to 27° C.). Bags were randomly sampled and analyzed to approximate the fungal colony forming units for each lot of inoculated granules. Briefly, a dilution series was made using sterile water amended with 0.1% v/v Tween 80. Aliquots of the dilutions were plated on potato dextrose agar supplemented with Rose Bengal and chlorotetracycline. Fungal colonies were counted after 3 to 5 days incubation at approximately 25° C. For combination treatments, inoculated granules were blended to achieve a 1:1 blend of the *P. bilaiae* isolates by titre.

Field plot establishment was specific to each site (see Table 1). Seed row spacing was 30 inches, with 2 rows of corn per plot plus two guard rows. Fertilization included a standard nitrogen fertility program (site specific), plus 10 kg ha$^{-1}$ P$_2$O$_5$ applied with the seed. Penicillium strains were formulated as peat granules and applied in furrow at a rate of 4.5 kg ha$^{-1}$ (2.07 to 2.17E+10 colony forming units ha$^{-1}$).

TABLE 1

Details of field plot establishment at four USA locations.

| Site | Seed variety | Seed size (g 100 kernels$^{-1}$) | Seeding rate (seeds ac$^{-1}$) | Plot size |
|---|---|---|---|---|
| Fergus Falls, MN | DK 40-07 | 21.25 | 34,000 | 10 × 20 ft |
| York, NE | Cornhusker Hybrids 1 | 28.33 | 33,000 | 525 ft$^2$ |
| Gardner, ND | Mycogen 2K154 | 32.66 | 32,000 | 7.3 × 30 ft |
| Centerville, SD | NK 51-T8 | 29.46 | 28,000 | 10 × 30 ft |

Combined trial analysis shows significantly higher corn yield in the *P. bilaiae* combination treatment compared to the uninoculated control (FIG. 1). The *P. bilaiae* combination out-yielded either of the *P. bilaiae* strains when used as a separate treatment. The *P. bilaiae* strain combination was the most impactful treatment on corn yield in these studies.

Example 3

Solubilization of Insoluble Phosphates

Phosphate solubilizing strains of *P. bilaiae* have been included in laboratory experiments examining the ability of these organisms to solubilize insoluble calcium phosphates. The experiment consisted of two strains of *P. bilaiae* singly and in combination at two different concentrations, as well as an uninoculated control.

Hydroxyapatite was weighed into 300-mL Erlenmeyer flasks at a rate of 100 mg P per flask. Minimal salts media was prepared as follows (g L$^{-1}$): 0.1 NaCl, 0.4 NH$_4$Cl, 0.78 KNO$_3$, 0.1 CaCl$_2$.2H$_2$O, 1.0 MgSO$_4$.7H$_2$O, 10.0 sucrose. 100 mL of media was added to each flask, and flasks were plugged with a foam stopper and autoclaved (121° C. and 1.2 atm for 30 min). Triplicate flasks were inoculated with liquid spore stocks to a target inoculation rate of 4.00E+06 spores per flask. For the *P. bilaiae* combination treatments, the flasks were inoculated either with 4.00E+06 spores of each strain per flask, or to a total spore concentration of 4.00E+06 spores per flask (i.e., 2.00E+06 spores per flask of each strain). Flasks were incubated at ambient room temperature on a rotary shaker set to 175 rpm. Subsamples were aseptically collected at 3, 5, 7, and 10 days after inoculation and analyzed for soluble phosphate using a malachite-green method.

Figure 2:
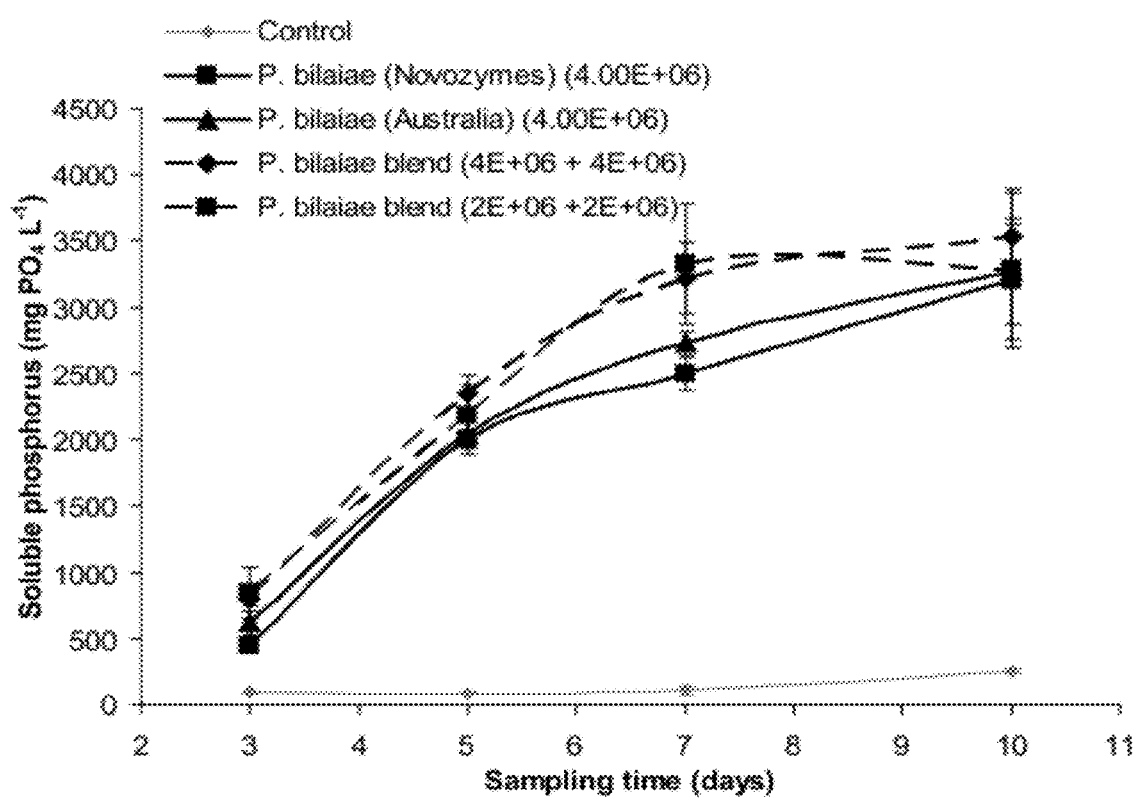
FIG. 2 shows hydroxyl apatite solubilisation in liquid culture by *P. bilaiae* strains singly and in combination. Numbers in brackets indicate incubation rate (spores per flask).

The combination of *P. bilaiae* strains was able to solubilize significantly more hydroxyapatite than either strain alone, as indicated by increased soluble phosphate levels, with rate of inoculation have little to no effect (FIG. 2).

Example 4

Growth Room Trials of Combination Treatment

Growth room trials were established in 2009 to screen the effect of inoculation with phosphate solubilizing strains of *P. bilaiae* on the dry matter accumulation of soybean and corn. Treatments included two strains of *P. bilaiae* singly and in combination as well as an uninoculated control.

The trials were established as randomized factorials with 8 replicates per trial. The two factors were phosphate fertilizer and inoculant. Fertilizer levels were equivalent to 0, 20, 40, and 80 lb P$_2$O$_5$ ac$^{-1}$ for soybean, and 0, 40, 80, and 160 lb P$_2$O$_5$ ac$^{-1}$ for corn. Inoculant treatments were composed of an uninoculated control, two single strain *Penicillium* treatments [NRRL 50169 (Novozymes P-201 strain) and NRRL 50162 (Australian P-208 strain)], and a double-strain treatment involving equal amounts of both *Penicillium* strains.

Plastic pots were labeled according to treatment and a sterile square of black landscape fabric was placed in the bottom of each to prevent the potting mix from leaking through the drainage holes. Pots were filled with a 1:1 mixture of industrial quartz sand and fine-milled vermiculite. Each pot was treated with the appropriate rate of phosphate suspension prepared using hydroxyapatite, sealed inside a Ziploc bag, and allowed to equilibrate for 7 days prior to seeding.

Inoculant treatments were applied as a liquid seed treatment. Cultures of *Penicillium* were taken from storage at −80° C. and grown on potato dextrose agar. Spores were collected by using a glass rod to scrape the surface of a sporulating culture (obtained after two weeks of incubation at room temperature) into sterile water amended with 0.1% v/v Tween 80. The spore suspensions were titred, mixed thoroughly, and added to seed lots pre-weighed into plastic bags at a rate of 1.50E+05 colony forming units per seed. For combination treatments, a 1:1 blend of *P. bilaiae* isolates was achieved by halving the volume of spore suspension required to reach the target inoculation rate for each strain (i.e., final inoculation rate remained 1.50E+05). Uninoculated control treatments were treated with sterile water. The plastic bags were sealed and shaken vigorously for 1 to 2 min to evenly coat the seeds. Bags were re-opened, and the seeds were allowed to dry for 20 to 30 min prior to planting.

Soybean and corn seeds were planted 5 per pot. Phosphate-free nutrient solution was added to pots at the time of seeding, and every two weeks for the duration of the experiment. Pots were placed into the growth room with day/night settings of 16/8 h and 20/15° C., and watered on as required. Pots were thinned to three seedlings one to two weeks after planting. Plants were harvested approximately 7 and 6 weeks after planting for soybean and corn, respectively. Shoots were removed above the soil line, placed inside pre-weighed paper bags, and dried for 10 d at 72° C. to determine the dry shoot weight.

Figure 3:
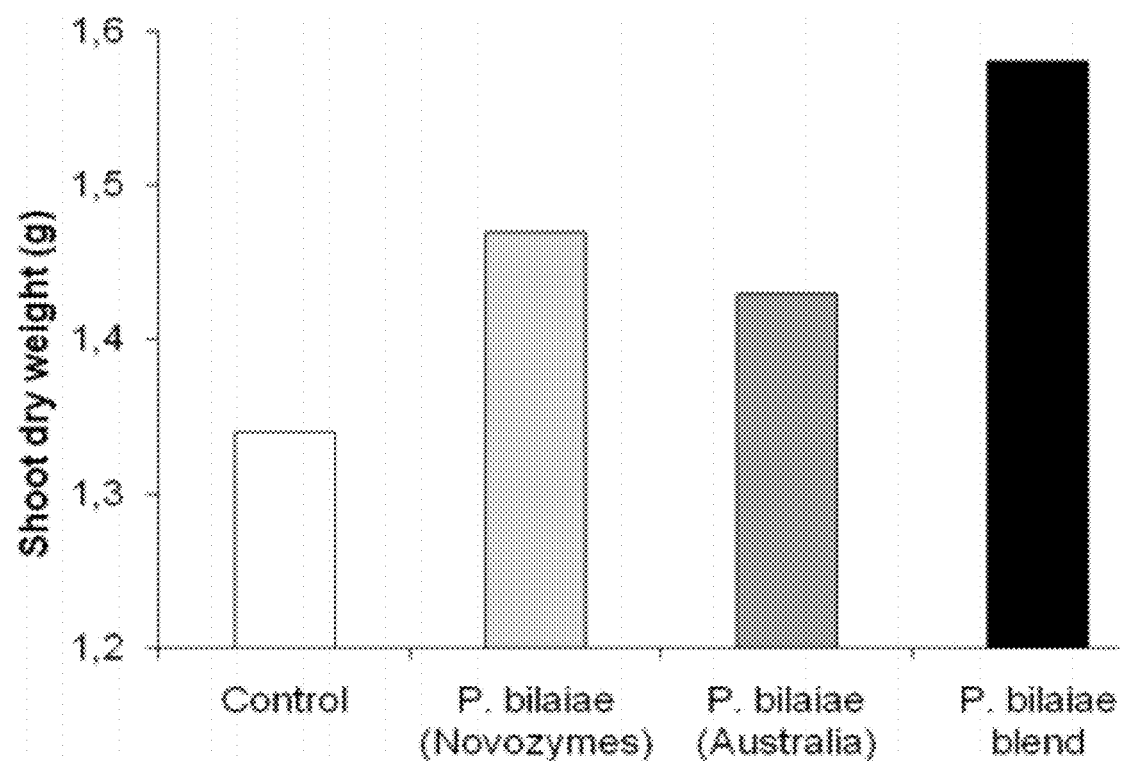
FIG. 3 shows the effect of inoculation with phosphate solubilising microorganisms on the shoot dry weight of soybean grown under growth room conditions. *P. bilaiae* (Novozymes) corresponds to strain NRRL 50169, *P. bilaiae* (Australia) corresponds to NRRL 50162, and *P. bilaiae* blend corresponds to a 1:1 blend of the two strains.

Across all fertilizer levels, soybean showed higher shoot dry matter accumulation in the *P. bilaiae* blend treatment compared to the uninoculated control (FIG. 3). The *P. bilaiae* blend treatment also performed better than either of the *P. bilaiae* strains alone.

Figure 4:
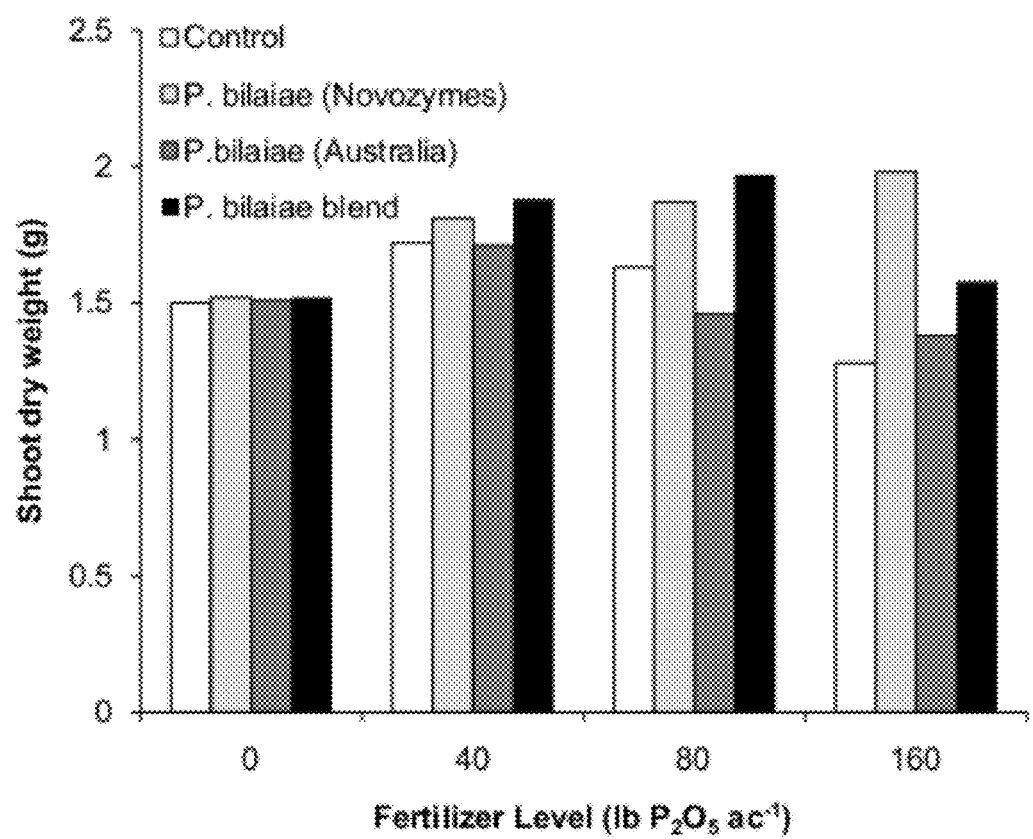
FIG. 4 shows the effect of inoculation with phosphate solubilizing microorganisms on shoot dry weight of corn grown under growth room conditions. *P. bilaiae* (Novozymes) corresponds to strain NRRL 50169, *P. bilaiae* (Australia) corresponds to NRRL 50162, and *P. bilaiae* blend corresponds to a 1:1 blend of the two strains.

Corn showed higher shoot dry matter accumulation in the *P. bilaiae* blend treatment than the uninoculated control for all fertilizer levels (FIG. 4). The *P. bilaiae* combination treatment also performed better than either of the *P. bilaiae* strains alone at the 40 and 80 lb P$_2$O$_5$ ac$^{-1}$ fertilizer rates.

Deposit of Biological Material

The following biological material has been deposited under the terms of the Budapest Treaty with the Agricultural Research Service Patent Culture Collection (NRRL), Northern Regional Research Center, 1815 N. University Street, Peoria, Ill., 61604, USA, and given the following accession number:

| Deposit | Accession Number | Date of Deposit |
|---|---|---|
| *Penicillium bilaiae* | NRRL 50169 | Aug. 28, 2008 |

The following biological material has been deposited under the terms of the Budapest Treaty with the Agricultural Research Service Patent Culture Collection (NRRL), Northern Regional Research Center, 1815 N. University Street, Peoria, Ill., 61604, USA, and given the following accession number:

| Deposit | Accession Number | Date of Deposit |
|---|---|---|
| *Penicillium bilaiae* | NRRL 50162 | Aug. 11, 2008 |

The following biological material has been deposited under the terms of the Budapest Treaty with Agricultural Research Service Patent Culture Collection (NRRL), Northern Regional Research Center, 1815 N. University Street, Peoria, Ill., 61604, USA and given the following accession number:

| Deposit | Accession Number | Date of Deposit |
|---|---|---|
| *Penicillium gaestrivorus* | NRRL 50170 | Aug. 28, 2008 |

The strains have been deposited under conditions that assure that access to the culture will be available during the pendency of this patent application to one determined by foreign patent laws to be entitled thereto. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention claimed is:

1. A method of increasing the availability of phosphorus for plant uptake from soil, which method comprises introducing into the soil inoculums of at least two different strains of the fungus *Penicillium* selected from the group consisting of *P. bilaiae, P. gaestrivorus*, and combinations thereof.

2. The method according to claim 1, wherein the *P. bilaiae* is selected from the group consisting of NRRL 50169, ATCC 20851, ATCC 22348, ATCC 18309, NRRL 50162.

3. The method according to claim 2, wherein the selected strains are NRRL 50169 and NRRL 50162.

4. The method according to claim 1, wherein a source of phosphorus is added to said soil.

5. The method according to claim 4, wherein said source is rock phosphate.

6. The method according to claim 4, wherein said source is a manufactured fertilizer.

7. The method according to claim 6, wherein said manufactured fertilizer is selected from the group consisting of monoammonium phosphate, triple super phosphate, diammonium phosphate, ordinary superphosphate and ammonium polyphosphate.

8. The method according to claim 4, wherein said phosphorus source is organic.

9. The method according to claim 8, wherein said organic source of phosphorus comprises bone meal, meat meal, animal manure, compost, sewage sludge, guano, or mixtures thereof.

10. The method according to claim 1, wherein said inoculums are added to the soil in an amount of $10^6$ to $10^{11}$ colony forming units per hectare.

11. The method according to claim 1, wherein said *Penicilium* fungus is introduced as a seed coating comprising $10^1$-$10^8$ colony forming units per seed.

12. The method according to claim 1, wherein the plants are selected from the group consisting of cereals, legumes, *Brassica* spp., fruits, vegetables, nuts, flowers, and turf.

13. The method according to claim 11, wherein said *Penicilium* fungus is introduced as a seed coating comprising $10^2$-$10^6$ colony forming units per seed.

14. A method of enhancing growth conditions of plants, which comprises growing the plants in soil containing, in proximity to the plant roots, both a phosphorus source and at least two strains identified by the deposit numbers NRRL 50169, NRRL 50162.

15. A composition for application to soil, which comprises: i) inoculums of at least two strains of the fungus *Penicillium* selected from the group consisting of *P. bilaiae, P. gaestrivorus*, and combinations thereof, and ii) a soil-compatible carrier for the fungus.

16. The composition according to claim 15, wherein said strains are identified by the deposit numbers NRRL 50169 and NRRL 50162.

17. The composition according to claim 15, in the form of a coating for plant seeds.

18. A plant seed having a coating comprising inoculums of at least two strains of the fungus *Penicillium* selected from the group consisting of *P. bilaiae, P. gaestrivorus*, and combinations thereof, and a solid soil-compatible carrier therefore.

19. The plant seed according to claim 18, wherein the *Penicillium* strains are identified by the deposit numbers NRRL 50169 and NRRL 50162.

* * * * *